United States Patent
Huang et al.

(10) Patent No.: US 9,428,802 B2
(45) Date of Patent: Aug. 30, 2016

(54) SELECTIVE-COMPETITIVE PRIMER AND METHOD OF USE

(75) Inventors: Jr-kai Huang, New Taipei (TW); Chi-Kuan Chen, Taichung (TW); Tao-Yeuan Wang, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 66 days.

(21) Appl. No.: 14/351,629

(22) PCT Filed: Jul. 3, 2012

(86) PCT No.: PCT/CN2012/078099
§ 371 (c)(1),
(2), (4) Date: Apr. 14, 2014

(87) PCT Pub. No.: WO2014/005278
PCT Pub. Date: Jan. 9, 2014

(65) Prior Publication Data
US 2015/0140564 A1    May 21, 2015

(51) Int. Cl.
*C12P 19/34* (2006.01)
*C12Q 1/68* (2006.01)

(52) U.S. Cl.
CPC ............. *C12Q 1/686* (2013.01); *C12Q 1/6858* (2013.01)

(58) Field of Classification Search
USPC .............................................. 435/6.12, 91.2
See application file for complete search history.

(56) References Cited

U.S. PATENT DOCUMENTS 6,015,675 A * 1/2000 Caskey ............... C07H 21/00
435/6.12

FOREIGN PATENT DOCUMENTS

CN        2424852 A    4/2012
WO   03027283 A1    4/2003

OTHER PUBLICATIONS

Chi-Kuan Chen, et al.; "Universal Insertion/deletion-enrich PCR"; Taiwanese Journal of Obstetrics and Gynecology, 2011, No. 50; pp. 499-502.

* cited by examiner

*Primary Examiner* — Kenneth Horlick
(74) *Attorney, Agent, or Firm* — Thomas Horstemeyer, LLP

(57) ABSTRACT

Disclosed herein is a self-competitive primer for preferentially amplifying a sample nucleic acid based on whether a selected region thereof has a nucleotide variation, in comparison with a selected region of a reference nucleic acid. The self-competitive primer includes a 5'-competing domain and a 3'-elongating domain. Sequences of the 5'-competing domain and the 3'-elongating domain are complementary to a first region and a second region of the reference nucleic acid, respectively. The first region includes the selected region and at least one nucleotide residue immediately downstream of the selected region of the reference nucleic acid. The second region is located downstream of the selected region of the reference nucleic acid and does not comprise the selected region of the reference nucleic acid, and the first region and the second region overlap by at least one nucleotide. Also disclosed herein is a method for preferentially amplifying a variant sample nucleic acid over a non-variant sample nucleic acid.

20 Claims, 4 Drawing Sheets

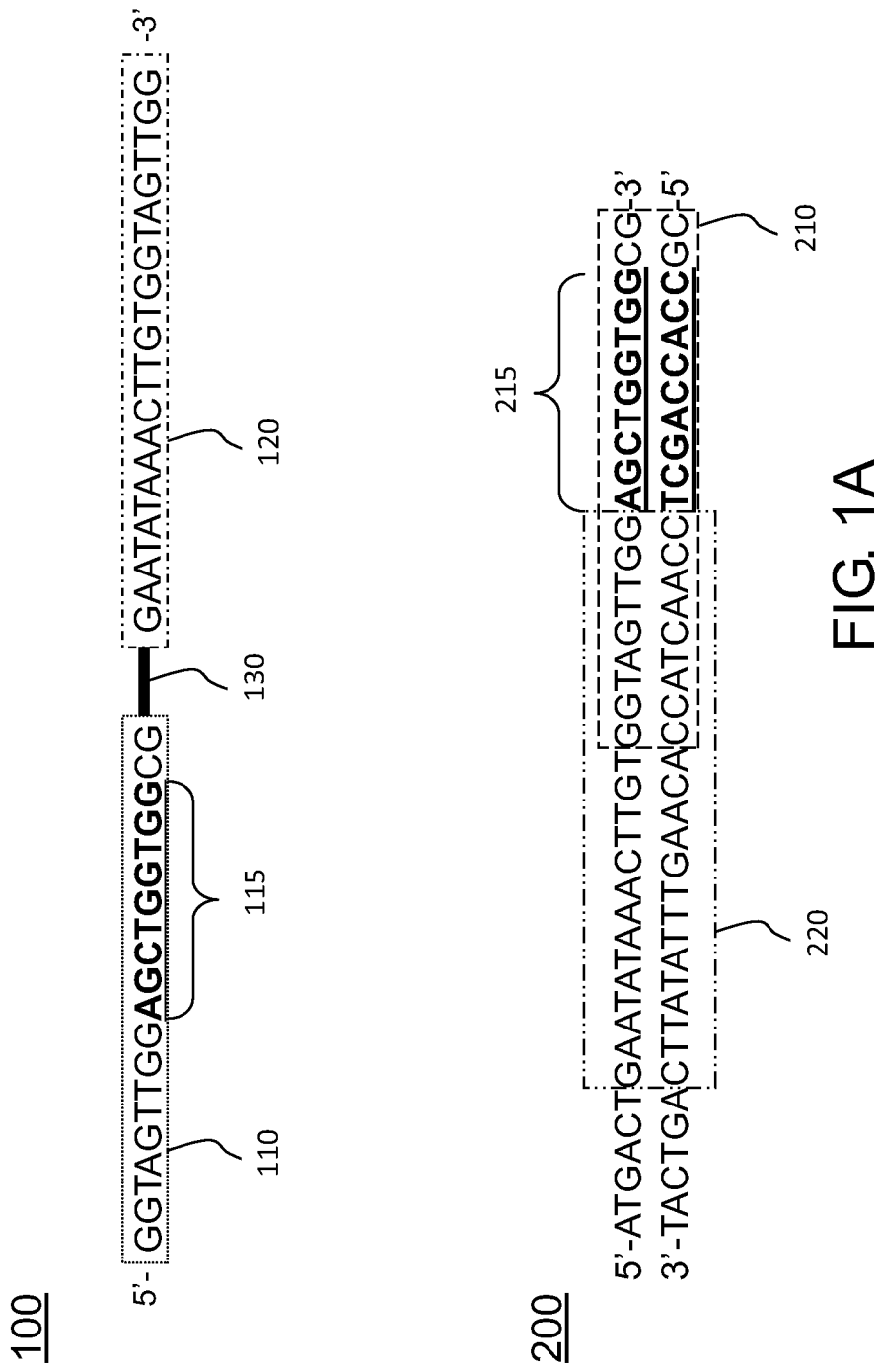

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ggtagttgga gctggtggcg                                                   20

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gaatataaac ttgtggtagt tgg                                               23

<210> SEQ ID NO 3
<211> LENGTH: 40
<212> TYPE: DNA
<213> ORGANISM: Homo sapiens

<400> SEQUENCE: 3
atgactgaat ataaacttgt ggtagttgga gctggtggcg                             40

<210> SEQ ID NO 4
<211> LENGTH: 40
<212> TYPE: DNA
<213> ORGANISM: Homo sapiens

<400> SEQUENCE: 4
cgccaccagc tccaactacc acaagtttat attcagtcat                             40

<210> SEQ ID NO 5
<211> LENGTH: 9
<212> TYPE: DNA
<213> ORGANISM: Homo sapiens

<400> SEQUENCE: 5 ccaccagct                                                                9

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
cctctattgt tggatcata                                                    19
```

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aggcctgctg aaaatgactg                                                      20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
accgtgcagc tcatcacgca g                                                    21

<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
ctcacctcca ccgtgca                                                         17

<210> SEQ ID NO 10
<211> LENGTH: 30
<212> TYPE: DNA
<213> ORGANISM: Homo sapiens

<400> SEQUENCE: 10
ctcacctcca ccgtgcagct catcacgcag                                           30

<210> SEQ ID NO 11
<211> LENGTH: 30
<212> TYPE: DNA
<213> ORGANISM: Homo sapiens

<400> SEQUENCE: 11
ctgcgtgatg agctgcacgg tggaggtgag                                           30

<210> SEQ ID NO 12
<211> LENGTH: 10
<212> TYPE: DNA
<213> ORGANISM: Homo sapiens

<400> SEQUENCE: 12
cgtgatgagc                                                                 10

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
caaactcttg ctatcccagg ag                                                   22

```
<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
gaaactcaag atcgcattca tg                                              22
```

SELECTIVE-COMPETITIVE PRIMER AND METHOD OF USE

CROSS-REFERENCE TO RELATED APPLICATION

This application is the 35 U.S.C. §371 national stage of PCT Application No. PCT/CN2012/078099, filed Jul. 3, 2012, which is herein incorporated by reference in its entirety.

BACKGROUND OF THE INVENTION

1. Field of the Invention

The present disclosure relates to primers and methods for detecting variant(s). More particularly, the present disclosure relates to a self-competitive primer for preferentially amplifying a sample nucleic acid having a nucleotide variation.

2. Description of Related Art

Gene mutations are alterations in the nucleotide sequence of a given gene or regulatory sequence from a naturally occurring or normal nucleotide sequence. A mutation may be a point mutation (single nucleotide substitution), a deletion or insertion mutation of one or more nucleotides, a substitution mutation of more than one nucleotide, or crossing-over in chromosomal level (translocation).

The identification of gene mutations or nucleotide variations is of great importance in molecular genetics. For example, many genes associated with the onset and/or progression of cancers have been identified, and thereby allows the development of molecular target therapies that specifically target these genes. In these target therapies, sequence variation of the targeted gene(s) may affect the efficacy of a given treatment. Therefore, the detection of gene mutation(s) in cancerous cells makes it possible to devise a treatment plan best suited the patient.

Various techniques for detecting gene mutations or nucleotide variations have been developed. For examples, mutated nucleotide(s) could be revealed by Sanger's direct sequencing of sequence of interest. However, the sensitivity of this technique is too low and the operation thereof requires considerable time and effort, thereby hindering its application in clinical and research uses.

Alternatively, primers and/or probes specific to the nucleotide variation could be used to positively detect such variation. Conventionally, primers or probes for detecting mutations are designed with prior knowledge of the sequence of the mutated site. For example, allele specific oligonucleotides-polymerase chain reaction (ASO-PCR) is often used for the detection of gene mutations. In ASO-PCR, a primer specific to the wild-type or the mutant sequence is used, and the presence or absence of a mutant sequence is judged by whether amplification may proceed. One disadvantage of ASO-PCR lies in that it generally has a low specificity thereby leading to a high false-positive rate. Moreover, the low specificity may result in mis-amplification of the sample nucleic acid, thereby producing amplicons having a sequence differing from the sample nucleic acid by introducing the primer sequence into the amplicons. The mis-amplification of the sample nucleic acid would render the subsequent confirmation step (such as sequencing) meaningless since the amplicon does not reflect the amplification of the genuine sequence of the sample nucleic acid. Further, in the ASO-PCR method, only one primer is allowed in one reaction system, and therefore, it is only possible to detect one sequence (either wild-type or mutant) once. Therefore, in the event where multiple nucleotide variations may occur at a same position, multiple primers shall be designed to ensure the full coverage of all mutated sequences, and separate reactions shall be conducted in order to correctively detect the mutation.

Another commonly used detection technique is ligase chain reaction (LCR), which is often utilized in conjunction with other amplification-based methods such as PCR. LCR employs a thermostable ligase and two sets of primers in which each primer set has two primers that are ligated together only when immediately adjacent to each other thereby allowing the discrimination of single nucleotide variation (such as point mutation, single-nucleotide deletion, and single-nucleotide insertion). Despite having various advantages, LCR is not capable of detecting a mutated sequence that has multiple-nucleotide variation.

Moreover, in the event of disease diagnosis, samples obtained from living tissue may contain cells having the wild-type sequence, as well as the mutated sequence. As could be appreciated, the wild-type cells often present in an excess amount with respect to mutated cells, which may obscure the amplification and thus the detection of the mutated sequence.

In view of the foregoing, there exists a need in the art for the development of a detection method capable of accurately detecting nucleotide variation, including both single-nucleotide and multiple-nucleotide variations.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure is based on, at least in part, a novel primer design scheme which allows the preferential amplification and thus detection of a variant, as compared with a reference nucleic acid.

In one aspect, the present disclosure is directed to a self-competitive primer for preferentially amplifying a sample nucleic acid based on whether the sample nucleic acid has or lacks a nucleotide variation in a selected region thereof, in comparison with a selected region of a reference nucleic acid.

According to one embodiment of the present disclosure, the self-competitive primer comprises a 5'-competing domain and a 3'-elongating domain. The 5'-competing domain comprises a sequence that is complementary to a first region of the reference nucleic acid, in which the first region comprises the selected region and at least one nucleotide residue immediately downstream of the selected region of the reference nucleic acid. The 3'-elongating domain comprises a sequence that is complementary to a second region of the of the reference nucleic acid, in which the second region is located downstream of the selected region of the reference nucleic acid and does not comprise the selected region of the reference nucleic acid, and the first region and the second region overlap by at least one nucleotide. The 3'-elongating domain serves as a forward primer for a polymerase chain reaction (PCR)-based amplification of the sample nucleic acid such that the sample nucleic acid having the nucleotide variation (i.e., a variant sample nucleic acid) is preferentially amplified over the sample nucleic acid lacking the nucleotide variation (i.e., a non-variant sample nucleic acid).

According to some embodiments of the present disclosure, the self-competitive primer may be a non-chimeric primer. In other alternative embodiments, the self-competitive primer may be a chimeric primer.

In various embodiments of the present disclosure, the last nucleotide of the 3'-elongating domain may be complementary to the nucleotide residues located 1-37 nucleotides downstream of the selected region of the reference nucleic acid.

According to some embodiments of the present disclosure, the 5'-competing domain and the 3'-elongating domain of the self-competitive primer are directly or indirectly linked by a 3'-5' linkage or a 5'-5' linkage. In the case where the two domains are directly linked, the self-competitive primer consists of the 5'-competing domain and the 3'-elongating domain.

In alternative embodiment, the self-competitive primer further comprises a nucleosidic linker or a non-nucleosidic linker joining the 5'-competing domain and the 3'-elongating domain. Non-limiting examples of non-nucleosidic linker may be a peptide, a carbohydrate, a lipid, a fatty acid, a C2-C18 alkyl linker, a phosphate group, a phosphate ester, a phosphoramidite, poly(ethylene glycol) linker, an ethylene glycol linker, a branched alkyl linker, glycerol, or a heterocyclic moiety. According to one example of the present disclosure, the non-nucleosidic linker is a C3 spacer.

In one embodiment, both the 5'-competing domain and the 3'-elongating domain are DNA sequences, and the two domains are linked by a C3 spacer.

For example, the 5'-competing domain has a sequence of GGTAGTTGGAGCTGGTGGCG (SEQ ID NO: 1), and the 3'-elongating domain has a sequence of GAATATAAACTTGTGGTAGTTGG (SEQ ID NO: 2).

In another example, the 5'-competing domain has a sequence of ACCGTGCAGCTCATCACGCAG (SEQ ID NO: 8), and the 3'-elongating domain has a sequence of CTCACCTCCACCGTGCA (SEQ ID NO: 9).

In another aspect, the present disclosure is directed to a PCR-based method for preferentially amplifying a sample nucleic acid based on whether the sample nucleic acid has a nucleotide variation in a selected region thereof, in comparison with a selected region of a reference nucleic acid.

According to one embodiment of the present disclosure, the method comprises an amplification step for amplifying the sample nucleic acid with a self-competitive primer according to the aspect/embodiments of the present disclosure such that the sample nucleic acid that has the nucleotide variation (i.e., a variant sample nucleic acid) is preferentially amplified over the sample nucleic acid that does not have the nucleotide variation (i.e., a non-variant sample nucleic acid).

In yet another aspect, the present invention is directed to a PCR-based method for determining whether a sample nucleic acid has a nucleotide variation in a selected region thereof, in comparison with a selected region of a reference nucleic acid.

According to one embodiment of the present invention, the method comprises steps of amplification and detection; in which the sample nucleic acid is amplified with a self-competitive primer according to the aspect/embodiments of the present disclosure to give an amplicon; and the presence or absence of nucleotide variation in the selected region of the sample nucleic acid is determined.

In one embodiment, the detection comprises steps of sequencing the amplicon. Additionally or alternatively, the detection comprises quantifying the amplicon having nucleotide variation in the selected region and/or the amplicon lacking nucleotide variation in the selected region.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIGS. 1A-1C are schematic diagrams illustrating the design scheme of the self-competitive primer according to one embodiment of the present disclosure.

DESCRIPTION

Figure 1B:
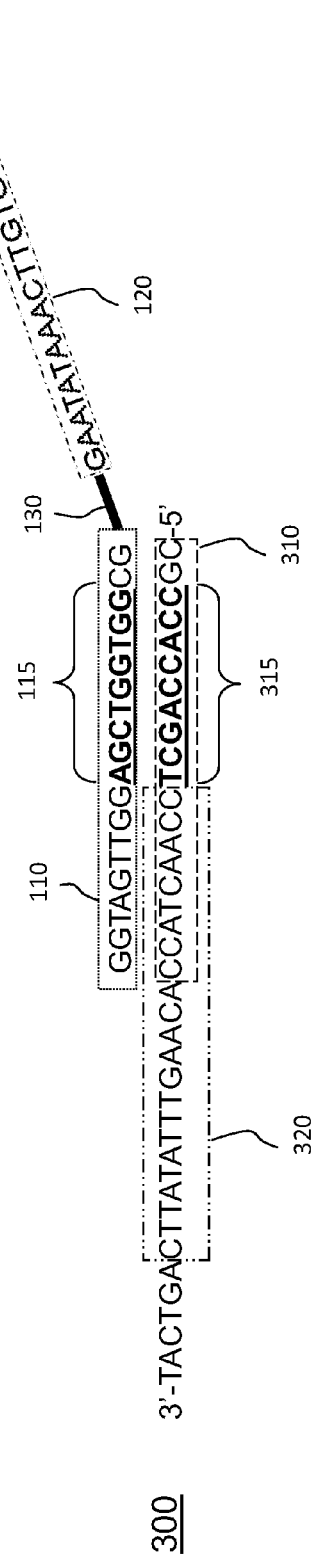
Figure 1B:
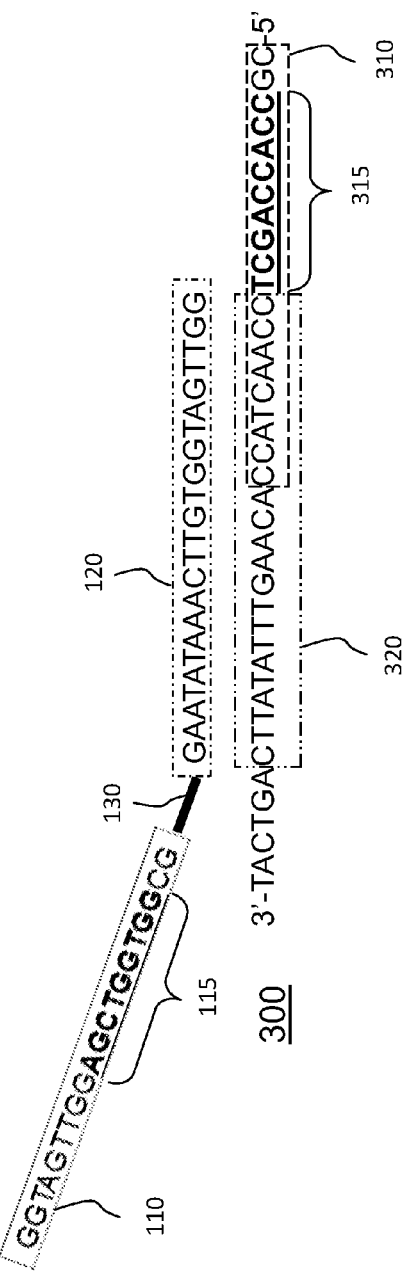

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "sample" refers to any sample containing nucleic acids. A sample may be a "biological sample" that includes or is formed of a cell, tissue, or component parts (e.g., body fluids) isolated from an animal or plant. Preferably, the animal may be a human. As used herein, biological samples include clinical samples derived from subjects in need of medical treatment. Exemplary biological samples include, but are not limited to, samples derived from blood, saliva, sputum, urine, feces, skin cells, hair follicles, semen, vaginal fluid, bone fragments, bone marrow, brain matter, cerebro-spinal fluid, amniotic fluid, and tissue biopsy. It should be noted that these examples are not to be construed as limiting the sample types applicable to the subject matter described herein.

The term "nucleic acid" refers to any chain of two or more nucleotides, nucleosides, or nucleobases (e.g., deoxyribonucleotides or ribonucleotides) covalently bonded together. Nucleic acids include, but are not limited to, viral genomes or portions thereof, either DNA or RNA, bacterial genomes or portions thereof, fungal, plant or animal genomes or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double-stranded or single-stranded form. The term "nucleotide" is a subunit of a nucleic acid and consists of a heterocyclic base, a sugar, and one or more phosphate groups. In the most common nucleotides, the base is a derivative of purine or pyrimidine, and the sugar is the pentose deoxyribose or ribose. The purines include adenine (A), and guanine (G); the pyrimidines include cytosine (C), thymine (T), and uracil (U).

As used herein, a "sequence" of a nucleic acid refers to the ordering of nucleotides which make up a nucleic acid. Throughout this application, nucleic acids are designated as having a 5' end and a 3' end. Unless specified otherwise, the left-hand end of a single-stranded nucleic acid is the 5' end; and the right-hand end of single-stranded nucleic acid is the 3' end. The term "downstream" refers to a nucleotide sequence that is located 3' to a previously mentioned nucleotide sequence. The term "upstream" refers to a nucleotide sequence that is located 5' to a previously mentioned nucleotide sequence.

As used herein, the term "variant" refers to a change of one or more nucleotides of a reference nucleic acid which includes the insertion of one or more new nucleotides, deletion of one or more nucleotides, and substitution of one or more existing nucleotides. Broadly, the term "nucleotide variation" as used herein includes point mutation, multiple mutation, single nucleotide polymorphism (SNP), deletion, insertion, and translocation.

The term "reference nucleic acid" is used herein to describe a nucleotide sequence having a known reference sequence of interest. The reference sequence may be a "wild-type" (or "non-mutated", or "normal") sequence that has no mutation in the selected region thereof. Alternatively, the reference sequence may be a mutated sequence. As could be appreciated by persons with ordinary skills in the art, for a reference nucleic acid that comprises a wild-type sequence in the selected region, the variant sample nucleic acid may be any mutated sequence. Alternatively, when the reference nucleic acid has a known mutated sequence in the selected region, the variant sample nucleic acid may be the wild-type sequence or any of other mutated sequences. In the case where the reference nucleic acid is present in double-stranded form, the sequence of either the coding strand or the template strand may be used as the reference sequence.

The term "sample nucleic acid" as used herein refers to a nucleotide sequence under investigation for the presence or absence of nucleotide variation(s) in a "selected region" thereof. In the case where the sample nucleic acid is in the form of a double-strand DNA that consists of a template strand and a complementary coding strand, the sequence of the coding strand is oriented in the 5' to 3' direction, whereas the sequence of the template strand is oriented in the 3' to 5' direction. As used herein, a "variant sample nucleic acid" has at least one nucleotide variation in the selected region thereof in comparison with the selected region of the reference sequence. In the present disclosure, a sample nucleic acid that has a sequence identical to the reference nucleic acid in the selected region is also referred to as a "non-variant sample nucleic acid".

The term "primer" as used herein refers to a single stranded nucleotide sequence which is capable of acting as a point of initiation of synthesis of a primer extension product, when placed under suitable conditions (e.g., buffer, salt, temperature, and pH) in the presence of nucleotides and an agent for nucleic acid polymerization (e.g., a DNA-dependent or RNA-dependent polymerase). Generally, sequence of the primer is substantially complementary to a nucleic acid strand to be copied, or at least comprises a region of complementarity sufficient for annealing to occur and extension in the 5' to 3' direction therefrom. The primer may be a DNA primer, RNA primer, or a chimeric DNA/RNA primer. Primers are generally, but not necessarily, short synthetic nucleic acids of about 12-100 nucleotides in length; preferably, about 30-60 nucleotides in length.

The terms "hybridization" and "annealing" are used interchangeably to refer to the formation of complexes between nucleotide sequences which are sufficiently complementary to form complexes (or hybrids) via Watson-Crick base pairing or non-canonical base pairing. The hybridization may take place between two DNA strands, two RNA strands, or one DNA and one RNA strand. The hybridization occurs under a variety appropriate conditions (e.g. temperature, pH, salt concentration, etc.) that are well known in the art of molecular biology.

As used herein, the term "amplification" refers to a method or process that increases the representation of a population of specific nucleotide sequences in a sample. Polymerase chain reaction or PCR is a well-known amplification process in the art and is discussed in more detail below. As used herein, the terms "reaction mixture" and "mixture" are used interchangeably to refer to components that are subjected to a polymerase chain reaction.

As used herein, "preferentially amplifying a variant sample nucleic acid" means that the amplification of a variant sample nucleic acid is promoted, whereas the amplification of a non-variant nucleic acid is hindered. It should be noted that, according to principles and spirits of the present disclosure, both the variant and non-variant sample nucleic acids, if present in the reaction mixture, would be amplified under the action of the self-competitive primer provided herein. However, the amplification efficiency of the variant sample nucleic acid is much higher than that of the non-variant sample nucleic acid due to the present primer design. Therefore, it is feasible to correctly amplify the variant sample nucleic acid to a detectable amount even though the variant sample nucleic acid only accounts for a minor fraction in relation to the non-variant sample nucleic acid in the reaction mixture.

In order to provide a method for preferentially amplifying (and thus detecting) sample nucleic acid having nucleotide variation(s) in the selected region thereof, a self-competitive primer having two domains (i.e., a 5'-competing domain and 3'-elongating domain) that respectively bind to different but overlapping regions of the sample nucleic acid are designed. Detailed information regarding this primer and said method is provided hereinbelow.

Self-Competitive Primer

Figure 1C:
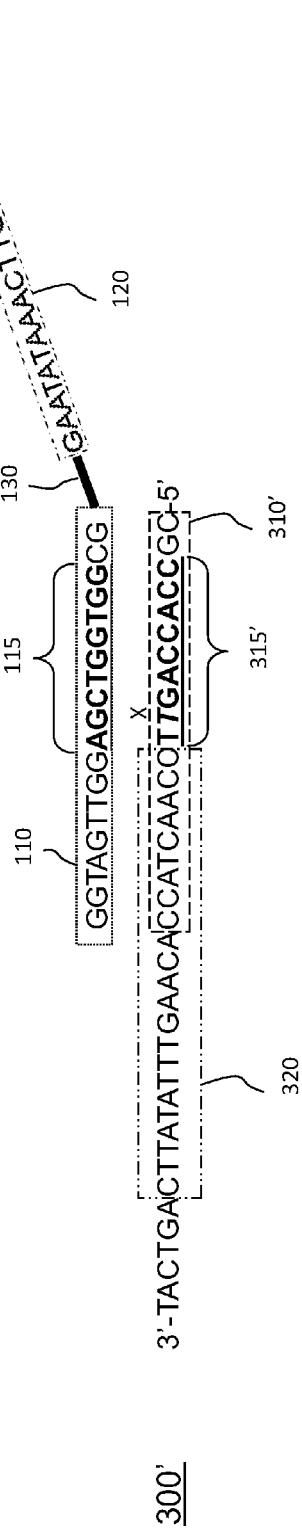
Figure 1C:
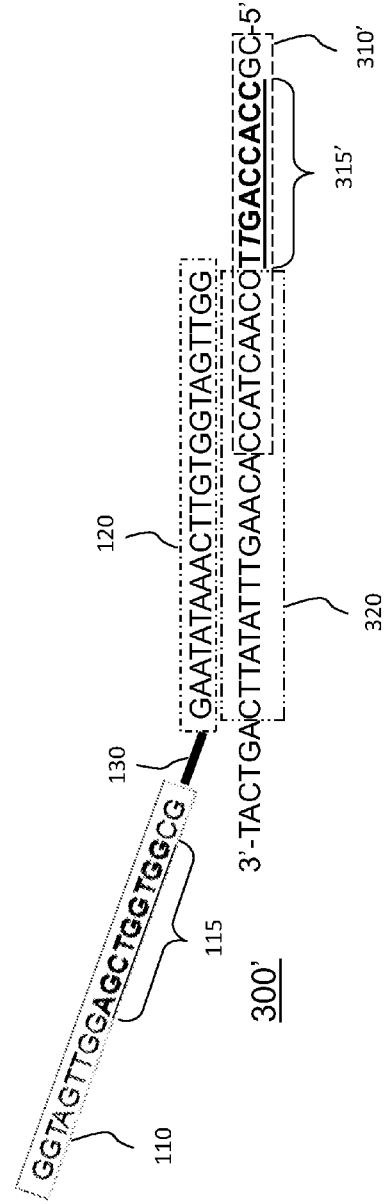

The primer design scheme is now discussed with reference to FIGS. 1A-1C to facilitate understanding of the present disclosure. It should be noted that sequences depicted in FIGS. 1A-1C are provided for the purpose of discussion and as examples, and thus, the claims that follow should not be limited in any way by these sequences.

In the example illustrated in FIG. 1A, the reference nucleic acid 200 comprises the $1^{st}$ to $40^{th}$ nucleotides of human KRAS (v-Ki-ras2 Kirsten rat sarcoma viral oncogene homolog) gene exon 1. The sequences of the coding and template strands of the reference nucleic acid 200 are respectively 5'-ATGACTGAATATAAACTTGTGGTAGT-TGGAGCTGGTGGCG-3' (SEQ ID NO: 3) and 3'-TACT-GACTTATATTTGAACACCATCAACCTCGACCAC-CGC-5' (SEQ ID NO: 4). For the purpose of discussion, the sequence of the template strand is used as the sequence of the nucleic acid 200 in the description that follows. In the context of present disclosure, the reference nucleic acid 200 has a selected region 215 which is under investigation for the presence or absence of nucleotide variation(s) in this selected region. In the present example, the selected region 215 of the reference nucleic acid 200 in the template strand has a sequence of 3'-TCGACCACC-5' (SEQ ID NO: 5, which corresponds to the $30^{th}$ to $38^{th}$ nucleotides of wild-type KRAS exon 1, indicated by bold and underlined in FIG. 1A).

Theoretically, the selected region to be investigated could have any number of nucleotides. According to optional embodiments of the present invention, the selected region may have about 20 nucleotides at maximum. For example, the length of the selected region may be about 1, 5, 10, 15, or 20 nucleotides.

In order to provide a method for detecting the nucleotide variation in the selected region, a self-competitive primer that has two domains respectively hybridizing with different but overlapping regions of the reference nucleic acid is designed. Detailed information regarding this self-competitive primer is provided hereinbelow.

The present self-competitive primer comprises a 5'-competing domain and a 3'-elongating domain, respectively complementary to a first region and a second region of a reference nucleic acid. The 3'-elongating domain serves as a forward primer for a polymerase chain reaction (PCR)-based amplification of the sample nucleic acid such that a sample nucleic acid that has the nucleotide variation (i.e., a variant sample nucleic acid) is preferentially amplified over a sample nucleic acid that does not have the nucleotide variation (i.e., a non-variant sample nucleic acid).

The first region comprises the selected region and at least one nucleotide residue immediately downstream of the selected region of the reference nucleic acid such that the 5'-competing domain may hybridize with the selected region and at least one adjacent nucleotide under appropriate hybridization conditions. Optionally, the nucleotide residues immediately downstream of the selected region may be at least 1 to 20 nucleotide residues. In another optional embodiment, the first region may further comprise at least one nucleotide residue immediately upstream the selected region. Still optionally, the nucleotide residues immediately upstream the selected region may be at least 1 to 20 nucleotide residues. According to certain embodiments of the present disclosure, the 5'-competing domain may be 15-40 nucleotides in length.

The exemplified self-competitive primer 100 as illustrated in FIG. 1A has a 5'-competing domain 110 having a sequence of GGTAGTTGGAGCTGGTGGCG (SEQ ID NO: 1, corresponding to the $21^{st}$ to $38^{th}$ nucleotides of wild-type KRAS exon 1, in which the selected region 115 is italicized in the specification, and indicated by bold and underlined in FIG. 1A). The sequence of the 5'-competing domain 110 is complementary to the sequence of a first region 210 of the reference nucleic acid 200, in which the first region 210 comprises the selected region 215, 9 downstream nucleotides, and two upstream nucleotides of the template strand of the reference nucleic acid 200.

The second region is located downstream of the selected region. Specifically, the 3'-end of the second region is located at least one nucleotide downstream of the 5'-end of the selected region, and therefore, the second region would not comprise the selected region of the reference nucleic acid. In optional embodiments, the 3'-end of the second region is located at least 1 to 20 nucleotides downstream of the 5'-end of the selected region. According to certain embodiments of the present disclosure, the 3'-elongating domain may be 15-40 nucleotides in length.

Moreover, the first region and the second region shall overlap each other by at least one nucleotide so as to promote the preferential amplification of the variant sample nucleic acid. In this way, the 3'-elongating domain and the 5'-competing domain, under appropriate hybridization conditions, may compete for the overlapping nucleotide(s) in order to hybridize with the sample nucleic acid. In some optional embodiments, the first region and the second region may overlap with each other by 1-38 nucleotides.

As illustrated in FIG. 1A, the exemplified 3'-elongating domain 120 has a sequence of GAATATAAACTTGTGG-TAGTTGG (SEQ ID NO: 2, corresponding to the $7^{th}$ to $29^{th}$ nucleotides of wild-type KRAS exon 1), which sequence is complementary to the second region 220 of the reference nucleic acid 200. Specifically, second region 220 comprises 23 consecutive nucleotide residues immediately downstream of the selected region 215 of the template strand of the reference nucleic acid 200. In this example, the last 9 nucleotides of the 3'-elongating domain 120 (starting from the 5'-end) are identical to the first 9 nucleotides of the 5'-competing domain 110 (also starting from the 5'-end).

According to various embodiments of the present invention, the 5'-competitive domain and the 3'-elongating domain may be joined via a conventional 3'-5' linkage or a less conventional 5'-5' linkage. The 5'-competitive domain and the 3'-elongating domain illustrated in FIG. 1A are linked via a 3'-5' linkage.

According to optional embodiments, the 5'-competitive domain is directly linked to the 3'-elongating domain. Alternatively, a linker may be introduced between the 5'-competitive domain and the 3'-elongating domain. The linker may be a nucleosidic linker or a non-nucleosidic linker. The nucleosidic linker consists of one or more nucleotides (e.g., A, T, C, G, or U, or other less common nucleotides). Non-limiting examples of non-nucleosidic linker may be a peptide, a carbohydrate, a lipid, a fatty acid, a C2-C18 alkyl linker, a phosphate group, a phosphate ester, a phosphoramidite (such as spacer phosphoramidite 9, spacer phosphoramidite 18, spacer phosphoramidite C3, spacer C12 CE phosphoramidite, and pyrrolidine-CE phosphoramidite), poly(ethylene glycol) linker, an ethylene glycol linker, a branched alkyl linker, glycerol, or a heterocyclic moiety. The self-competitive primer 100 depicted in FIG. 1A has a non-nucleosidic linker 130 (spacer phosphoramidite C3) linking the 3'-end of the 5'-competing domain 110 and the 5'-end of the 3'-elongating domain 120.

According to certain embodiments, the present self-competitive primer may be a non-chimeric primer in which the 5'-competing domain, the 3'-elongating domain and the nucleosidic linker (if any) are all deoxyribonucleotide sequences or ribonucleotide sequences. For example, the self-competitive primer 100 as illustrated in FIG. 1A is a non-chimeric primer because both the 5'-competing domain 110 and the 3'-elongating domain 120 consist of DNA bases, and the primer 100 does not contain a nucleosidic linker.

In some alternative embodiments, the self-competitive primer may be a chimeric primer in which one of the 5'-competing domain, the 3'-elongating domain, and the nucleosidic linker (if any) is of a different type of nucleotide sequence from the others. As illustrative examples, a chimeric self-competitive primer may take one of the following forms: a DNA 5'-competing domain directly linked to an RNA 3'-elongating domain, a DNA 5'-competing domain indirectly linked to an RNA 3'-elongating domain via a non-nucleosidic linker or a nucleosidic linker, an RNA 5'-competing domain directly linked to a DNA 3'-elongating domain, an RNA 5'-competing domain indirectly linked to a DNA 3'-elongating domain via a non-nucleosidic linker or a nucleosidic linker, a DNA 5'-competing domain indirectly linked to a DNA 3'-elongating domain via an RNA linker, or an RNA 5'-competing domain indirectly linked to an RNA 3'-elongating domain via a DNA linker, etc.

It should be noted that the present self-competitive primer is designed in such a way that the elongation—the addition of nucleotides to the new DNA strand—only begins at the 3'-end of the 3'-elongating domain, whereas the elongation using the 5'-competing domain as the starting point would be inhibited. For a 5'-competing domain and a 3'-elongating domain joined by a conventional 3'-5' linkage, the elongation starting from the 5'-competing domain is inhibited since the 3'-hydroxy group of the last nucleotide of the 5'-competing domain is not available.

In addition, the use of the above-mentioned chimeric self-competitive primer is also effective in inhibiting the elongation starting from the 5'-elongation domain. It is well known that polymerases may be categorized into DNA-dependent or RNA-dependent polymerases based on the type of template sequence. Hence, for a chimeric self-competitive primer, the inhibition of elongation from the 5'-competing domain may be achieved by selecting a polymerase based on the type of the 3'-elongating domain. For example, if the 5'-competing domain consists of RNA bases while the 3'-elongating domain consists of DNA bases, a DNA-dependent polymerase would only initiate elongation from the 3'-end of the 3'-elongating domain. Similarly, for a chimeric self-competitive primer having a 5'-competing domain consisting of DNA bases while a 3'-elongating domain consisting of RNA bases, a RNA-dependent polymerase could be used for initiating the elongation from the 3'-elongating domain.

Yet another exemplary approach introduces a less conventional 5'-5' linkage between the 5'-competing domain and the 3'-elongating domain of the present self-competitive primer. In this case, the 3'-end of the 5'-competing domain should be modified to prevent the elongation therefrom when the self-competitive primer is a non-chimeric primer. As to a chimeric self-competitive primer, modification of the 3'-end of the 5'-competing domain to prevent the elongation therefrom is not a requisite. The 3'-end of the 5'-competing domain may be modified by a non-nucleosidic blocker, such as a phosphate group, or a phosphate ester. For example, the 3'-propyl phosphate formed using 3'-Spacer C3 controlled pore glass (CPG) is one of the effective non-nucleosidic blocker of the 3'-terminus. Having a single inverted base at the 3' position of the last nucleotide of the 5'-competing domain with a 3'-3' linkage also prevents nucleotide extension by polymerases as there is no free 3' hydroxyl group to initiate synthesis. Another way to avoid polymerase extension at the 3'-end of the 5'-competing domain is using a nucleosidic blocker such as a 2',3'-dideoxynucleoside (e.g., 2',3'-ddC-CPG) or a 3'-deoxynucleoside (e.g., 3'-dA-CPG, 3'-dC-CPG, 3'-dG-CPG, or 3'-dT-CPG). These and other equivalent techniques for modifying the 3' end of the 5'-competing domain are envisioned and all should be considered to be within the scope of the present disclosure.

Another exemplary self-competitive primer used in the working example below is designed based on the above-mentioned design scheme with respect to human epidermal growth factor receptor (EGFR) gene. The self-competitive primer comprises a 5'-competing domain having a sequence of ACCGTGCAGCTCATCACGCAG (SEQ ID NO: 8), a C3 spacer, and a 3'-elongating domain having a sequence of CTCACCTCCACCGTGCA (SEQ ID NO: 9).

Method for Preferentially Amplifying Variant Sample Nucleic Acid over Non-variant Sample Nucleic Acid Now that the present primer design scheme and an exemplary self-competitive primer have been discussed in detail, attention is directed to the PCR-based preferential amplification method using such self-competitive primer.

As could be appreciated by persons having ordinary skills in the art, a biological sample subjected to amplification may contain both the wild-type sequence and the mutated sequence regarding a specific target gene. For example, in a sample harboring from the tissue, such as a lesion or site of disease (e.g., tumor), of an organism, some mutated cells might exist therein. In this case, the amount of the mutated sequence only accounts for a minor fraction in relation to the wild-type sequence, and most conventional PCR methods could not correctly amplify the mutated sequence to an amount that is sufficient for subsequent sequencing or other qualitative analysis. One novel feature in the present disclosure lies in that the present self-competitive primer may allow for the preferential amplification of the variant sample nucleic acid (such as the mutated sequence in a biological sample) over the non-variant sample nucleic acid (such as the wild-type sequence in the same biological sample) such that the variant sample nucleic acid would be amplified to an extent sufficient for sequencing or detection. In other words, the scarcity of the variant sequence will not pose any difficulty in detection according to the present invention. This is of particular advantage as in areas such as oncology in which the genetic makeup of the cancerous cell is often an indicator of the progression status of the tumor and/or the suitable therapeutic approach. Results from our working examples revealed that in a sample containing both the wild-type and mutated sequences, the present method is capable of detecting the mutated sequence even when the amount of mutated sequence is much lesser than the amount of the wild-type sequence.

According to one embodiment of the present disclosure, the PCR-based method for preferentially amplifying a variant sample nucleic acid over a non-variant sample nucleic acid comprises an amplification step for amplifying the sample nucleic acid with a self-competitive primer (such as, but not limited to, the self-competitive primer 100) according to the above-mentioned aspect/embodiments of the present disclosure. Specifically, the amplification step comprises preparing a reaction mixture comprising the self-competitive primer and the sample nucleic acid, and them subjecting the reaction mixture to a PCR process. Generally, the sample nucleic acid may or may not have a nucleotide variation in relative to the reference nucleic acid within the selected region. According to the principles and spirits of the present disclosure, the present method is applicable in situations where the variant sequence is known or unknown. For example, the sample may contain the non-variant sample nucleic acid 300 and variant sample nucleic acid 300' illustrated in FIG. 1B and FIG. 1C, respectively. The non-variant nucleic acid 300 has a first region 310 (including the selected region 315) and a second region 320 that are respectively identical to the first region 210 (including selected region 215) and second region 220 of the reference nucleic acid illustrated in FIG. 1A. The selected region 315 of the variant nucleic acid 300' differs from the selected region 215 of the reference nucleic acid by one nucleotide (indicated by bold, underline, and italic in FIG. 1C). Hence the sequence of the first region 310' of the variant sample nucleic acid 300' is not identical to the sequence of the first region 210 of the reference nucleic acid 200 or the first region 310 of the non-variant sample nucleic acid 300. However, the sequence of the second region 320 of the variant sample nucleic acid 300' is identical to the sequence of the second region 220 of the reference nucleic acid 200 or the second region 320 of the non-variant sample nucleic acid 300.

As could be appreciated by persons with ordinary skills in the art, the reaction mixture may further comprise other amplification reaction reagents. These amplification reaction reagents are used in PCR and may include, but are not limited to, buffers, reagents, enzymes having reverse transcriptase and/or polymerase activity or exonuclease activity; enzyme cofactors such as magnesium or manganese; salts; and deoxynucleotide triphosphates (dNTPs) such as deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP). Amplification reaction reagents may readily be selected by one skilled in the art depending on the PCR process used.

The reaction mixture is then subjected to a PCR process. For sample nucleic acid that is double-stranded, the PCR process comprises, sequentially in steps, a denaturing step, an annealing step, and an extension step.

In the denaturing stage, the double-stranded nucleic acid formed by the template strand and the coding strand are denatured (i.e., melted). The precise denaturing behavior of the double-stranded nucleic acid is unique to its size, sequence, and molecular composition (primarily, the ratio of guanine-cytosine bonds to adenine-thymine bonds, or G-C %). The denaturing of double-stranded nucleic acid occurs in less than one second, at temperatures from about 80° C. or lower (for small targets with a low G-C %) to about 95° C. (for human genomic DNA).

After the denaturing stage, the reaction mixture is cooled to an annealing temperature so that the 5'-competing domain and the 3'-elongating domain of the self-competitive primer compete to anneal to one strand of the sample nucleic acid (in this example, the template strand). It would be appreciated by any skilled artisan that the hybridizing sequences need not have perfect complementarity. Therefore, the 5'-competing domain 110 may hybridize with the template strand of the non-variant sample nucleic acid 300 as well as with the template strand of the variant sample nucleic acid 300' (see, both FIG. 1B and FIG. 1C). However, the hybrid formed between the 5'-competing domain 110 and the variant sample nucleic acid 300' would be less stable in relative to the hybrid formed between the 5'-competing domain 110 and the non-variant sample nucleic acid 300, and thus the hybrid of the 5'-competing domain 110 and the variant sample nucleic acid 300' tends to denature thereby leaving the 3'-elongating domain 120 a greater possibility to anneal with such variant sample nucleic acid 300', as compared with the possibility of the annealing between the 3'-elongating domain 120 and the non-variant sample nucleic acid 300. Therefore, during the subsequent extension step, the amplification of the variant sample nucleic acid 300' may be promoted, whereas the amplification of the non-variant sample nucleic acid 300 would be hindered. The increased amplification efficiency of the variant sample nucleic acid sequence in combination with the decreased amplification efficiency of the non-variant sample nucleic acid sequence in a single reaction system would result in the preferential amplification of the variant sample nucleic acid sequence.

In an optional embodiment, the annealing step comprises two stages in which a first annealing temperature is higher than a second annealing temperature.

After the annealing step, the mixture is subjected to the extension temperature which allows the extension of nucleotides. Optimal extension temperatures are well-known in the prior art. Generally, the extension temperature is between about 70-80° C. However, other temperatures may be used depending on factors such as the polymerase that are used.

The reaction mixture is then cycled through the denaturing, annealing, and extension steps to allow the amplification of the sample nucleic acid (both variant and non-variant). The present PCR-based preferential amplification method may be carried out in any known PCR thermocycler and equivalents thereof. Further, the present method is compatible with most of the conventional PCR procedures. Therefore, it is possible to adapt the present method for various PCR techniques, which include but are not limited to asymmetric PCR, hot start PCR, miniprimer PCR, multiplex-PCR, nested PCR, real-time quantitative PCR, reverse transcription PCR, solid phase PCR, and touchdown PCR.

For example, the cycling conditions used in a working example were, denaturing at about 95° C. for about 10 min, 45 cycles of about 94° C. for about 60 sec (denaturing), about 60° C. for about 60 sec (annealing), about 72° C. for about 60 sec (extension), and final extension at about 72° C. for about 10 minutes. In another working example (data not shown), the cycling conditions included, denaturing at about 95° C. for about 10 min, followed by 45 cycles of about 94° C. for about 60 sec (denaturing), about 65° C. for about 180 sec (the first annealing), about 57° C. for about 60 sec (the second annealing), about 72° C. for about 60 sec (extension), and final extension at about 72° C. for about 10 minutes.

In another aspect, the present invention is directed to a PCR-based method for determining whether a sample nucleic acid has a nucleotide variation in a selected region thereof, in comparison with a selected region of a reference nucleic acid.

According to one embodiment of the present invention, the method comprises an amplification step and a detection step. The amplification step is carried out in accordance with the PCR-based method preferential amplification method described above. Then, in the detection step, the presence or absence of nucleotide variation in the selected region of the sample nucleic acid is determined.

For example, the PCR product from the amplification step could be sequenced to confirm the sequence(s) of the sample nucleic acid in the sample.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE I

Preferential Amplification of Variant KRAS Gene Fragment

A total of 153 clinical samples were collected from the lesion site of cancer patients in Mackay Memorial Hospital (Taiwan) with informed consent. Samples were processes to isolate nucleic acid. In an initial experiment, the PCR-based preferential amplification was performed using the following ingredients, PCR Buffer2X Master mix (JMR) 10 µl, 0.2 µM self-competitive primer (5'-competing domain: SEQ ID NO: 1; linker: C3 spacer; 3'-elongation domain: SEQ ID NO: 2), 0.2 µM reverse primer (CCTCTATTGTTGGAT-CATA, SEQ ID NO: 6), template DNA 100 ng, and water to a final volume of 20 µl. Conventional PCR amplification was also conducted using a conventional PCR forward primer (AGGCCTGCTGAAAATGACTG, SEQ ID NO: 7) using the same protocol. The cycling conditions used in the reaction were, denaturing at 95° C. for 10 min, 45 cycles of 94° C. for 60 sec, 60° C. for 60 sec, 72° C. for 60 sec, and final extension at 72° C. for 10 minutes in ABI 9700 PCR machine.

After the completion of the PCR reaction, a sample was taken from the PCR pouch and electrophoresis was performed on an agarose gel, along with the tube control. The gels were imaged using fluorescence detection with ethidium bromide (EtBr) and a CCD camera detector. Product bands shown on the gel were excised, and the nucleic acids contained therein were sequenced to determine whether the sample contained a mutated variant. The sequencing results indicated that a total of 12 mutated variants in the selected region of the KRAS gene (the $30^{th}$ to $38^{th}$ nucleotide residues of exon 1) were preferentially amplified (and thus made detectable) by the present PCR-based preferential amplification method; the mutated sequences of theses KRAS variants and positions thereof are summarized in Table 1. The wild type KRAS fragment comprises the sequence of SEQ ID NO: 3 (coding strand), which are the $1^{st}$ to $40^{th}$ nucleotides of KRAS gene exon 1.

TABLE 1

| Mutant No. | Nucleotide position | Mutated nucleotide |
| --- | --- | --- |
| 1 | 30 | A > T |
| 2 | 31 | G > A |
| 3 | 31 | G > C |
| 4 | 34 | G > A |
| 5 | 34 | G > T |
| 6 | 34 | G > C |
| 7 | 35 | G > A |
| 8 | 35 | G > T |
| 9 | 35 | G > C |
| 10 | 37 | G > A |

TABLE 1-continued

| Mutant No. | Nucleotide position | Mutated nucleotide |
| --- | --- | --- |
| 11 | 37 | G > T |
| 12 | 38 | G > A |

Results from conventional PCR amplification and the present preferential amplification were compared, and the data were summarized in Table 2. It should be noted that in Table 2, the mutant KRAS samples may contain both the mutated KRAS sequence and the wild-type KRAS sequence or only the mutated KRAS sequence, whereas the wild-type KRAS samples contained only the wild-type KRAS sequence.

Of the 69 samples that were confirmed to be KRAS mutant by direct sequencing, only 54 samples were detected as KRAS mutant using conventional PCR, while 15 of the 99 samples suggested to be wild-type KRAS samples by conventional PCR were confirmed to be KRAS mutant samples based on the direct sequencing of the product from preferential amplification. These results indicated that conventional PCR has a false positive percentage of about 15% and a detection sensitivity of about 78% in detecting KRAS mutation.

By contrast, all KRAS mutant and wild-type samples were correctly detected by the present preferential amplification method (false positive: 0%; false negative: 0%; sensitivity: 100%). According to this example, the preferential amplification provided by the present invention is useful in detecting variants in a sample such as a clinical sample.

TABLE 2

| | Conventional PCR | | Preferential Amplification | |
| --- | --- | --- | --- | --- |
| | Mutant (+) | Wild (−) | Mutant (+) | Wild (−) |
| Mutant (+) | 54 | 15 | 69 | 0 |
| Wild (−) | 0 | 84 | 0 | 84 |
| Total | 54 | 99 | 69 | 84 |
| False Positive | 0% | | 0% | |
| False Negative | 15% | | 0% | |
| Sensitivity | 78% | | 100% | |

Figure 2:
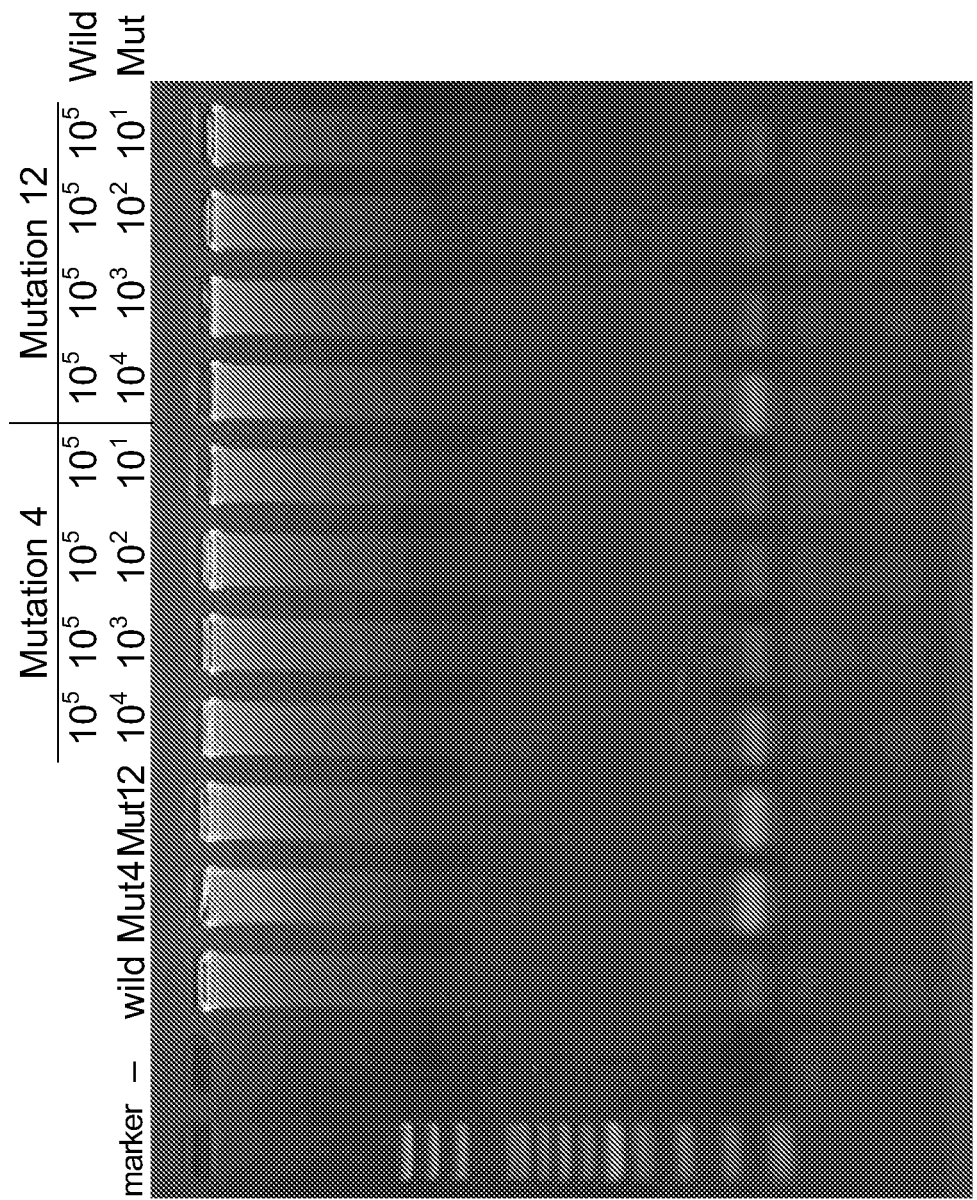
FIG. 2 is a photograph showing the electrophoresis results of preferential amplification of the variant sequence according to one example of the present disclosure.

Stock solutions of purified plasmid DNA containing the KRAS mutants and the wild-type KRAS sequence were respectively prepared to give a final concentration of about $10^5$ DNA copies per microliter. Stocks containing the KRAS mutant sequence were serially diluted over 4 logs (i.e., $10^2$-$10^5$ copy/µl), and then each diluted stock (1 µl) was mixed with the KRAS wild-type stock ($10^5$ copy/µl, 9 µl) and used as the template for preferential amplification following the above-described protocol. FIG. 2 is a photograph illustrating the electrophoresis results of the mutant 4 and mutant 12 of Table 1.

As could be seen in FIG. 2, the pure wild-type KRAS sample, as well as the pure mutant KRAS samples, would be amplified by the present preferential amplification method. In FIG. 2, the first and second lanes from the left are marker and negative control, respectively. It is noticeable that in FIG. 2 the intensities of the pure mutant KRAS samples (the fourth and fifth lanes from the left) were higher than the intensity of the pure KRAS wild-type sample (the third lane from the left). These results confirm the preferential amplification of the variant sample sequence over the non-variant sample sequence.

For templates containing both of the wild-type KRAS sequence and one mutant KRAS sequence (mutant 4 or 12), the mutant KRAS sequence was preferentially amplified over the wild-type KRAS sequence such that the mutant KRAS sequence was amplified to an amount sufficient for the subsequent direct sequencing. As is apparent from FIG. 2, the intensities of the product bands were increased gradually as the concentrations of the mutant KRAS sequence sequentially increased (see, the sixth to ninth lanes and the tenth to thirteenth lanes from the left). Since the concentrations of the wild-type KRAS sequence in these samples were the same, the increased intensity also confirms the preferential amplification of the variant (in this example, the mutant KRAS) sequence.

EXAMPLE II

Preferential Amplification of Variant EGFR Gene Fragment

A total of 179 clinical samples were collected from the lesion site of cancer patients in Mackay Memorial Hospital (Taiwan) with informed consent. Samples were processes to isolate nucleic acid. In an initial experiment, the PCR-based preferential amplification was performed using the following ingredients, PCR Buffer2X Master mix (JMR) 10 μl, 0.2 μM self-competitive primer (5'-competing region: SEQ ID NO: 8; linker: C3 spacer; 3'-elongation sequence: SEQ ID NO: 9), 0.2 μM reverse primer (CAAACTCTTGCTATC-CCAGGAG, SEQ ID NO: 13), template DNA 100 ng, and water to final volume of 20 μl. Conventional PCR amplification was also conducted using a conventional PCR forward primer (GAAACTCAAGATCGCATTCATG, SEQ ID NO: 14) using the same protocol. The cycling conditions used in the reaction were the same as those described in Example I, above.

In this example, the wild type EGFR fragment ($2344^{th}$ to $2373^{rd}$) had the sequences of SEQ ID NO: 10 (5'-CTCAC-CTCCACCGTGCAGCTCATCACGCAG-3'; coding strand) and SEQ ID NO: 11 (3'-GAGTGGAGGTG-GCACGTCGAGTAGTGCGTC-5'; template strand), and the selected region (the $2361^{st}$ to $2370^{th}$ nucleotide residues) of the EGFR fragment had a sequence of 3'-CGAG-TAGTGC-5' (SEQ ID NO: 12).

After the completion of the PCR reaction, the amplicon was processed in accordance with steps set forth in Example I hereinabove, and the sequencing results indicated that a total of 5 mutated variants in the selected region of the EGFR gene (the $2361^{st}$ to $2370^{th}$ nucleotide residues) were preferentially amplified (and thus made detectable) by the present PCR-based preferential amplification method; the mutated EGFR sequences of theses variants and positions thereof are summarized in Table 3.

TABLE 3

| Nucleotide position | Mutated nucleotide |
|---|---|
| 2361 | G > A |
| 2364 | C > T |
| 2367 | C > T |
| 2369 | C > T |
| 2370 | G > A |

Results from conventional PCR amplification and the present preferential amplification were compared, and the data were summarized in Table 4. It should be noted that in Table 4, the mutant EGFR samples may contain both the mutated EGFR sequence and the wild-type EGFR sequence or only the mutated EGFR sequence, whereas the wild-type EGFR samples contained only the wild-type EGFR sequence.

TABLE 4

| | Conventional PCR | | Preferential Amplification | |
|---|---|---|---|---|
| | Mutant (+) | Wild (−) | Mutant (+) | Wild (−) |
| Mutant (+) | 60 | 25 | 85 | 0 |
| Wild (−) | 0 | 94 | 0 | 94 |
| Total | 60 | 119 | 85 | 94 |
| False Positive | 0% | | 0% | |
| False Negative | 21% | | 0% | |
| Sensitivity | 66% | | 100% | |

Of the 85 samples that were confirmed to be EGFR mutant by direct sequencing, only 60 samples were detected as EGFR mutant using conventional PCR, while 25 of the 119 samples suggested to be wild-type EGFR samples by conventional PCR were confirmed to be mutant EGFR samples based on the direct sequencing of the product from preferential amplification. These results indicated that conventional PCR has a false positive percentage of about 21% and a detection sensitivity of about 66% in detecting EGFR mutation.

By contrast, all mutant and wild-type EGFR samples were correctly detected by the present preferential amplification method (false positive: 0%; false negative: 0%; sensitivity: 100%). According to this example, the preferential amplification provided by the present invention is useful in detecting variants in a sample such as a clinical sample.

In view of the foregoing, the present invention provides a novel self-competitive primer, which may allow for the amplification of both the wild-type and mutant sequences in a sample. This is beneficial because samples obtained from the lesion or site of disease often contain both the wild-type and mutant sequences with the former being by far the more abundant one, yet the present invention allows the correct amplification of the mutated sequence. For example, some samples used in Example I and Example II were collected from the lesion site of cancer patients, and these samples only contain a minor fraction of the mutated sequence in relation to the wild-type sequence. Under this circumstance, conventional PCR often fails to amplify the mutated sequence to an amount that is sufficient for direct sequencing or other means for confirming the presence of the mutated sequence. However, our experimental results revealed that while conventional PCR could not correctly detect all mutant samples, the present preferential amplification method provided a false-positive-free and false-negative-free detection means with 100% sensitivity. Also, the present invention is advantageous in that the preferential amplification provides a sensitive detection means with an improved detection limit.

In addition, since the 3'-elongating domain does not overlap with the selected region, the possibility of mis-amplification (in which the sequence of the amplicon in the selected region differs from the genuine sequence of the sample due to the PCR process) is minimal, if not zero. This feature is of particular importance in the case where the exact sequence (or phenotype) of a target gene or gene fragment is desired, because the occurrence of mis-amplified amplicons may jeopardize the reliability of the analysis and render the subsequent sequencing meaningless. For example, in the field of target therapy, treatment is tailored based on the exact sequence of the targeted gene of a subject or fragments thereof; hence, mis-amplification that give rise to amplicons that do not reflect the genuine sequence of the target gene of the subject may subsequently result in ineffective treatments.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A self-competitive primer for preferentially amplifying a sample nucleic acid based on whether the sample nucleic acid has or lacks a nucleotide variation in a selected region thereof, in comparison with a selected region of a reference nucleic acid, comprising,
 a 5'-competing domain comprising a sequence that is complementary to a first region of the reference nucleic acid, wherein the first region comprises the selected region and at least one nucleotide residue immediately downstream of the selected region of the reference nucleic acid; and
 a 3'-elongating domain comprising a sequence that is complementary to a second region of the reference nucleic acid, wherein the second region is located downstream of the selected region of the reference nucleic acid and does not comprise the selected region of the reference nucleic acid, and the first region and the second region overlap by at least one nucleotide, and wherein the 3'-elongating domain serves as a forward primer for a polymerase chain reaction (PCR)-based amplification of the sample nucleic acid whereby the sample nucleic acid having the nucleotide variation is preferentially amplified over the sample nucleic acid lacking the nucleotide variation.

2. The self-competitive primer of claim 1, wherein the self-competitive primer is a non-chimeric primer.

3. The self-competitive primer of claim 1, wherein the self-competitive primer is a chimeric primer.

4. The self-competitive primer of claim 1, wherein the 5'-competing domain and the 3'-elongating domain are directly or indirectly linked by a 3'-5' linkage or a 5'-5' linkage.

5. The self-competitive primer of claim 1, wherein the self-competitive primer consists of the 5'-competing domain and the 3'-elongating domain.

6. The self-competitive primer of claim 1, further comprising a linker joining the 5'-competing domain and the 3'-elongating domain.

7. The self-competitive primer of claim 6, wherein the linker is a non-nucleosidic linker selected from the group consisting of a peptide, a carbohydrate, a lipid, a fatty acid, a C2-C18 alkyl linker, a phosphate group, a phosphate ester, a phosphoramidite, a poly(ethylene glycol) linker, an ethylene glycol linker, a branched alkyl linker, glycerol, and a heterocyclic moiety.

8. The self-competitive primer of claim 6, wherein the linker is a nucleosidic linker.

9. The self-competitive primer of claim 6, wherein
 the self-competitive primer is a non-chimeric primer in which both the 5'-competing domain and the 3'-elongating domain are deoxyribonucleic acid sequences; and
 the linker is a C3 alkyl linker.

10. The self-competitive primer of claim 1, wherein the reference nucleic acid is a gene associated with a cancer or a hereditary disease, or a fragment thereof.

11. A PCR-based method for preferentially amplifying a sample nucleic acid based on whether the sample nucleic acid has or lacks a nucleotide variation in a selected region thereof, in comparison with a selected region of a reference nucleic acid, comprising amplifying the sample nucleic acid with a self-competitive primer comprising,
 a 5'-competing domain comprising a sequence that is complementary to a first region of the reference nucleic acid, wherein the first region comprises the selected region and at least one nucleotide residue immediately downstream of the selected region of the reference nucleic acid; and
 a 3'-elongating domain comprising a sequence that is complementary to a second region of the reference nucleic acid, wherein the second region is located downstream of the selected region of the reference nucleic acid and does not comprise the selected region of the reference nucleic acid, and the first region and the second region overlap by at least one nucleotide, and wherein the 3'-elongating domain serves as a forward primer for the PCR-based amplification of the sample nucleic acid whereby the sample nucleic acid having the nucleotide variation is preferentially amplified over the sample nucleic acid lacking the nucleotide variation.

12. The PCR-based method of claim 11, wherein the self-competitive primer is a non-chimeric primer.

13. The PCR-based method of claim 11, wherein the self-competitive primer is a chimeric primer.

14. The PCR-based method of claim 11, wherein the 5'-competing domain and the 3'-elongating domain are directly or indirectly linked by a 3'-5' linkage or a 5'-5' linkage.

15. The PCR-based method of claim 11, wherein the self-competitive primer consists of the 5'-competing domain and the 3'-elongating domain.

16. The PCR-based method of claim 11, further comprising a linker joining the 5'-competing domain and the 3'-elongating domain.

17. The PCR-based method of claim 16, wherein the linker is a non-nucleosidic linker selected from the group consisting of a peptide, a carbohydrate, a lipid, a fatty acid, a C2-C18 alkyl linker, a phosphate group, a phosphate ester, a phosphoramidite, poly(ethylene glycol) linker, an ethylene glycol linker, a branched alkyl linker, glycerol, and a heterocyclic moiety.

18. The PCR-based method of claim 16, wherein the linker is a nucleosidic linker.

19. The PCR-based method of claim 16, wherein
the self-competitive primer is a non-chimeric primer in which both the 5'-competing domain and the 3'-elongating domain are deoxyribonucleic acid sequences; and
the linker is a C3 alkyl linker.

20. The PCR-based method of claim 11, wherein the reference nucleic acid is a gene associated with cancer or a hereditary disease, or a fragment thereof.

* * * * *